United States Patent
Okamura (10) Patent No.: US 8,943,883 B2
(45) Date of Patent: Feb. 3, 2015

(54) APPARATUS FOR COUNTING MICROPARTICLES USING A GAS RESERVOIR TO INCREASE STABILITY OF AIR PRESSURE

(75) Inventor: Masakazu Okamura, Kanagawa (JP)

(73) Assignee: HGST Netherlands B.V., Amsterdam (NL)

( * ) Notice: Subject to any disclaimer, the term of this patent is extended or adjusted under 35 U.S.C. 154(b) by 330 days.

(21) Appl. No.: 13/617,456

(22) Filed: Sep. 14, 2012

(65) Prior Publication Data
US 2014/0076025 A1    Mar. 20, 2014

(51) Int. Cl.
*G01M 9/00*    (2006.01)

(52) U.S. Cl.
USPC .......................................................... 73/147

(58) Field of Classification Search
None
See application file for complete search history.

(56) References Cited

U.S. PATENT DOCUMENTS

| | | | |
|---|---|---|---|
| 4,530,272 A | 7/1985 | Stokes | |
| 6,863,362 B2* | 3/2005 | Reichel et al. | 347/19 |
| 7,010,991 B2 | 3/2006 | Lutz et al. | |
| 7,034,549 B2 | 4/2006 | Richardson, Jr. et al. | |
| 7,246,532 B2 | 7/2007 | Kim et al. | |
| 7,303,727 B1* | 12/2007 | Dubrow et al. | 422/503 |
| 7,430,046 B2 | 9/2008 | Jiang et al. | |
| 7,673,638 B1 | 3/2010 | Boynton et al. | |
| 7,738,099 B2 | 6/2010 | Morrell et al. | |
| 2004/0112980 A1* | 6/2004 | Reichel et al. | 239/102.1 |
| 2009/0118139 A1* | 5/2009 | Dunne et al. | 506/11 |
| 2011/0163469 A1* | 7/2011 | Little et al. | 264/9 |
| 2012/0234178 A1* | 9/2012 | Murai et al. | 96/283 |
| 2014/0008307 A1* | 1/2014 | Guldiken et al. | 210/748.05 |

FOREIGN PATENT DOCUMENTS

JP    10-090161    4/1998

OTHER PUBLICATIONS

Chunyong, Wang et al., "Hardware Implementation of High-Speed Data Aquisition and Buffering", http://en.cnki.com.cn/Article_en/CJFDTOTAL-DZCL200701032.htm.

* cited by examiner

*Primary Examiner* — Lisa Caputo
*Assistant Examiner* — Jermaine Jenkins (57) ABSTRACT

A microparticle count apparatus that includes or is connected to a gas reservoir for increasing stability of air pressure at the microparticle counter even when air pressure or air flow rate provided by a nozzle coupled to the microparticle measurement apparatus is unstable.

23 Claims, 5 Drawing Sheets

APPARATUS FOR COUNTING MICROPARTICLES USING A GAS RESERVOIR TO INCREASE STABILITY OF AIR PRESSURE

TECHNICAL FIELD

Embodiments of the present invention relate to apparatuses for counting microparticles

BACKGROUND

Dust particles can damage electronic items, such as magnetic disk drives or semi-conductors. For example, with the currently extremely narrow fly height requirements, even the smallest of particles can cause damage to a disk. Electronic items, such as these, are manufactured in a clean room to prevent and reduce the amount of dust particles that the electronic items are exposed to.

Therefore, during the process of manufacturing an electronic item, a microparticle measurement apparatus can be used to determine the amount of dust particles inside the clean room or on the surface of the electronic item. Gas can pass through the microparticle measurement apparatus to collect and count dust particles in order to estimate the amount of dust particles that have adhered to the electronic item as a part of quality control measurements. Action can be taken to reduce the amount of dust particles if the quality control measurements indicate that the amount of dust particles is above an acceptable threshold.

BRIEF DESCRIPTION OF THE DRAWINGS

The accompanying drawings, which are incorporated in and form a part of this specification, illustrate embodiments of the invention and, together with the description, serve to explain the principles of the invention.

The drawings referred to in this description should not be understood as being drawn to scale except if specifically noted.

DETAILED DESCRIPTION

Figure 1:
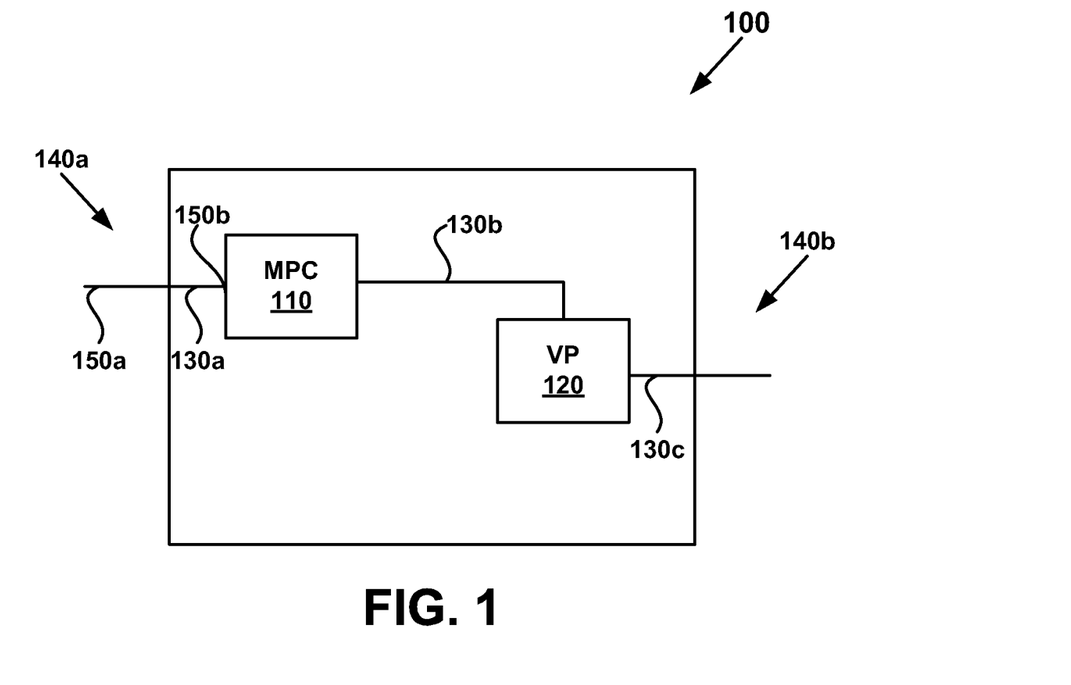
FIG. 1 depicts a block diagram of a conventional negative-pressure microparticle measurement apparatus.

FIG. 1 depicts a block diagram of a conventional negative-pressure microparticle measurement apparatus 100. The conventional negative-pressure microparticle measurement apparatus 100 includes a microparticle counter 110, a vacuum pump 120, a first gas pathway portion 130a at the gas inlet side 140a, a second gas pathway portion 130b between the microparticle counter 110 and vacuum pump 120, and a third gas pathway portion 130c at the gas outlet side 140b. One or more tubes, among other things, can be used as a part of implementing a gas pathway portion. End 150b of the first gas pathway portion 130a is connected air tightly to the microparticle counter 110.

Although a gas pathway portion may appear to go through the wall of a component, a gas pathway portion may be implemented, for example, using two tubes that are coupled on each side of that component's wall.

Figure 2:
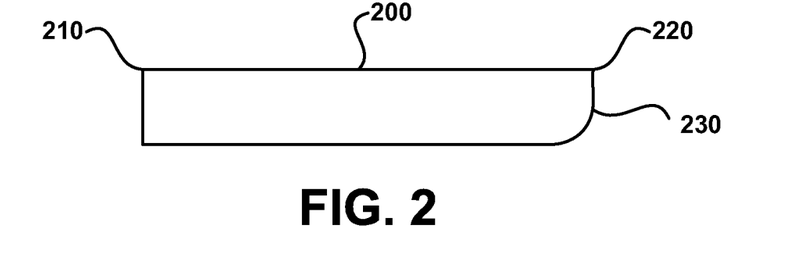
FIG. 2 depicts a nozzle, according to one embodiment.

A nozzle 200, as depicted in FIG. 2, may be attached to the other end 150a of the first gas pathway portion 130a. For example, the nozzle's end 210 can be connected to the first gas pathway portion's end 150a. Typically, the attachment of these respective ends 150a, 210 is air tight.

In measuring the amount of dust particles on the surface of an electronic item, the tip of the nozzle 200 is brought into proximity of the electronic item's surface. Normally, there is a gap between the electronic item's surface and the nozzle 200's tip 220. If the nozzle 200's tip 220 is too far from the electronic item's surface, the measurement that is take will not be a measurement of the item's surface but instead includes a measurement of the gas, such as air, in the clean room, thus, producing an inaccurate measurement.

On the other hand, if the nozzle 200's tip 220 is brought too close to the electronic item's surface, the gap becomes too narrow, restricting the nozzle 200's opening 230, which causes gas resistance to increase inside of the microparticle counter 110 and fluctuations in the air pressure and the air flow rate. The fluctuations in the air pressure and air flow rate may be extreme if the nozzle 200's tip 220 is very close to the electronic item's surface. The fluctuations in the air pressure and the air flow rate result in inaccurate dust particle measurements. Further, the life span of the conventional negative-pressure microparticle measurement apparatus 100 may be reduced by the fluctuations.

Differences in the shape of the nozzle 200's tip 220 can increase the differences in how different technicians perform measurements, further, increasing the difference in the size of the gap between the nozzle 200's tip 220 and the electronic item's surface from one measurement to another measurement. For example, different technicians may hold the nozzle 200's tip 220 close or further away from an electronic item's surface or may orient the nozzle 200's tip 220 different with respect to an electronic item's surface.

According to one embodiment, a negative-pressure-type microparticle measurement apparatus is provided that stabilizes air pressure at the location of the microparticle counter, even when there are fluctuations in the air flow rate supplied from the nozzle 200. According to one embodiment, increasing the stability of the air pressure and air flow rate makes it easier to more accurately count the number of dust particles in a volume of gas received by the apparatus' microparticle counter.

Figure 3:
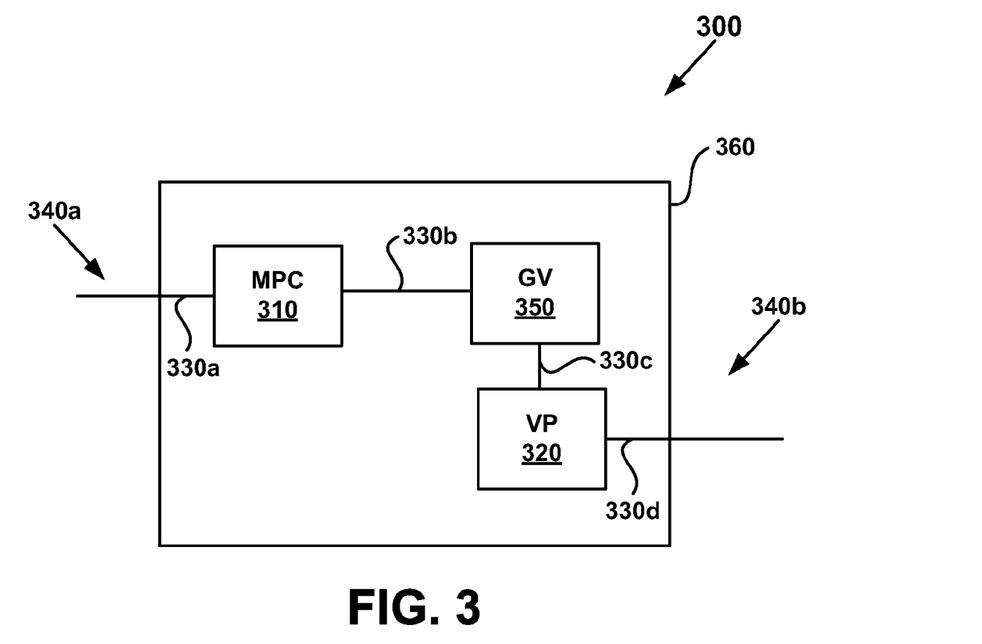
FIG. 3 depicts a block diagram of microparticle measurement apparatus, according to one embodiment.

FIG. 3 depicts a block diagram of microparticle measurement apparatus 300, according to one embodiment. As depicted in FIG. 3, the microparticle measurement apparatus 300 includes a microparticle counter 310, a gas reservoir 350, a vacuum pump 320 and apparatus 360. The microparticle counter 310, the gas reservoir 350, and the vacuum pump 320 are inside of the apparatus 360.

The first, second, third, and fourth gas pathway portion 330ds are a part of a gas pathway of the apparatus 300. One end of a first gas pathway portion 330a is connected to the apparatus 300's enclosure 360 at the inlet side 340a, the other end of the first gas pathway portion 330a is connected to a microparticle counter 310. One end of a second gas pathway potion is connected to the microparticle counter 310 and the other end of the second gas pathway portion 330b is connected to the gas reservoir 350. One end of a third gas pathway portion 330c is connected to the gas reservoir 350 and the other end of the third gas pathway portion 330c is connected to the vacuum pump 320. One end of a fourth gas pathway portion 330d is connected to the vacuum pump 320 and the other end of the fourth gas pathway portion 330d is connected to the apparatus 300's enclosure 360 at the outlet side 340b.

The vacuum pump 320 causes a volume of gas, such as air, to flow through the apparatus 300 by creating negative pressure. For example, the negative pressure caused by the vacuum pump 320 causes the volume of gas to be sucked into a nozzle's tip, pass through the first gas pathway portion 330a at the inlet side 340a to the microparticle counter 310, through the second gas pathway portion 330b to the gas reservoir 350, through the vacuum pump 320, through the third gas pathway portion 330c and out the apparatus 300 at the outlet side 340b. The gas reservoir 350, according to one embodiment, is inside the apparatus 300's enclosure 360. According to one embodiment, the gas reservoir 350 is between the microparticle counter 310 and the vacuum pump 320. The gas reservoir 350, according to one embodiment, increases the stability of air pressure at the microparticle counter 310 even when air pressure or air flow rate provided by a nozzle coupled to the microparticle measurement apparatus 300 is unstable.

Although a gas pathway portion may appear to go through the wall of a component, a gas pathway portion may be implemented, for example, using two tubes that are coupled on each side of that component's wall.

Figure 4:
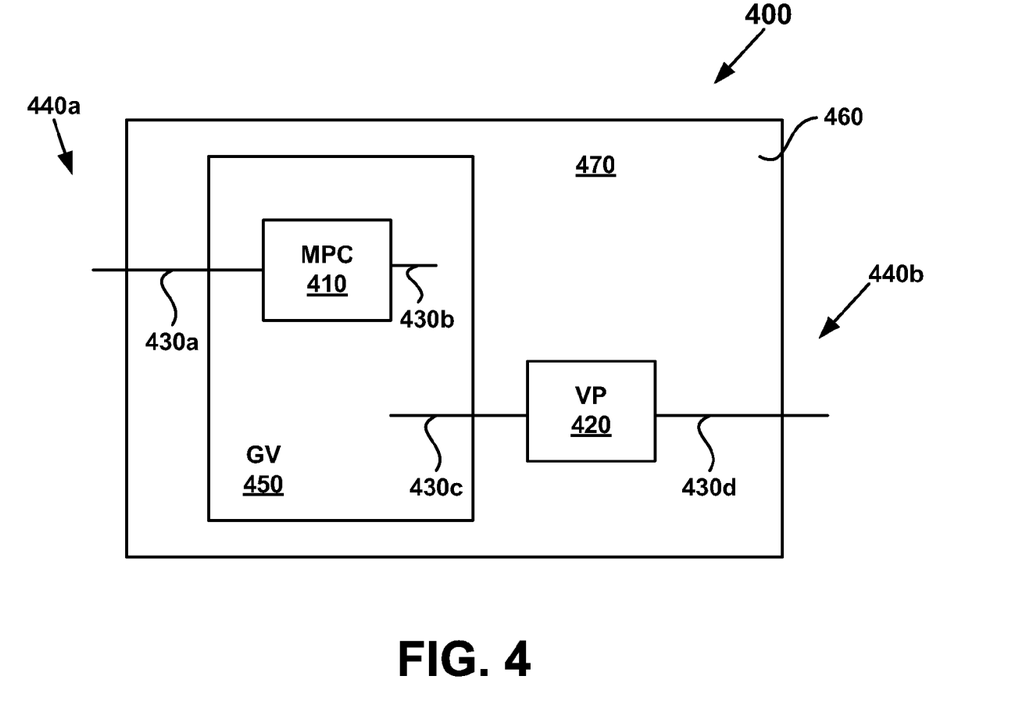
FIG. 4 depicts a block diagram of a microparticle measurement apparatus, according to one embodiment.

FIG. 4 depicts a block diagram of a microparticle measurement apparatus 400, according to one embodiment. As depicted in FIG. 4, the apparatus 400 includes a microparticle counter 410, a gas reservoir 450, a vacuum pump 420, and enclosure 460. The microparticle counter 410, the gas reservoir 450, and the vacuum pump 420 are inside of the enclosure 460. The gas reservoir 450 as depicted in FIG. 4 is inside of the microparticle counter 410.

The first, second, third, and fourth gas pathway portions 430 are a part of a gas pathway of the apparatus 400. One end of the first gas pathway portion 430a, located at the apparatus 400's inlet side 440a, is connected to the apparatus 400's enclosure 460, goes through the wall of the microparticle counter 410 and is connected to the gas reservoir 450. One end of the second gas pathway portion 430b is connected to the gas reservoir 450 and the other end is not connected to any component and is inside of the microparticle counter 410. One end of the third gas pathway portion 430c is not connected to any component and is inside of the microparticle counter 410. The other end of the third gas pathway portion 430c goes through the wall of the microparticle counter 410 and is connected to the vacuum pump 420. One end of the fourth gas pathway portion 430d is connected to the vacuum pump 420 and is connected to the apparatus 400's enclosure 460 at the inlet side 440b.

According to one embodiment, the gas reservoir 450 is at least partially air tight. According to one embodiment, the portion 470 of the apparatus 400 that is inside of the apparatus 400's enclosure 460 but outside of the microparticle counter 410 and vacuum pump 420 is not air tight. As depicted in FIG. 4, the second gas pathway portion 430b and the third gas pathway portion 430c are not connected to each other. For example, each of the second and third gas pathway portion 430cs has a respective end inside of the gas reservoir 450 and not connected to any component.

Figure 5:
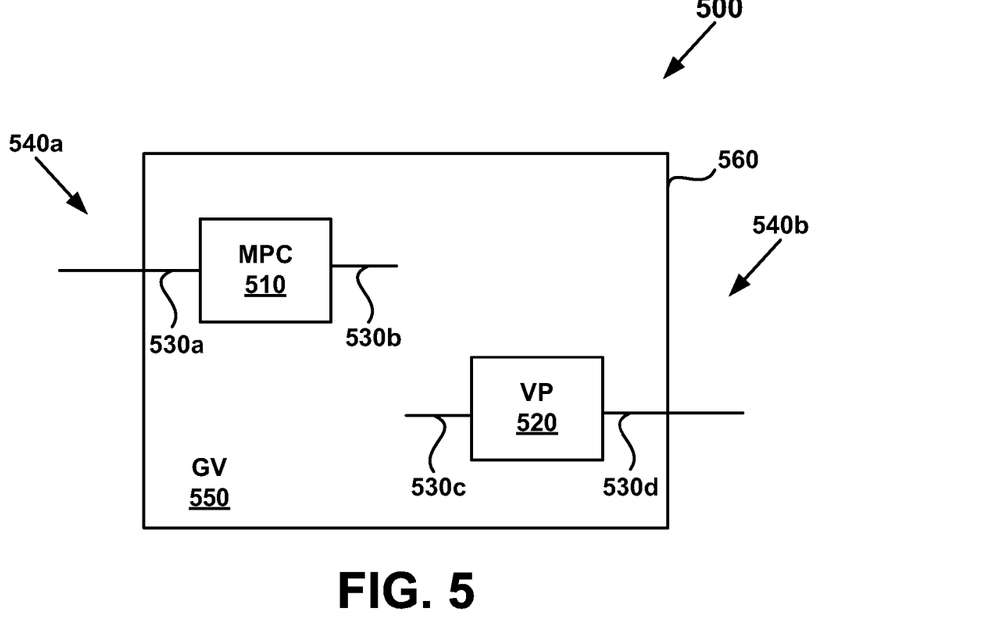
FIG. 5 depicts a block diagram of a microparticle measurement apparatus, according to one embodiment.

FIG. 5 depicts a block diagram of a microparticle measurement apparatus 500, according to one embodiment. As depicted in FIG. 5, the apparatus 500 includes a microparticle counter 510 and a gas reservoir 550 and enclosure 560. The microparticle counter 510, the gas reservoir 550, and the vacuum pump 520 are inside of the enclosure 560. As depicted in FIG. 5, the gas reservoir 550 is inside of the apparatus 500's enclosure 560 and is formed by the interior surface of the apparatus 500' enclosure 560.

The first, second, third, and fourth gas pathway portions 530 are a part of a gas pathway of the apparatus 500. One end of the first gas pathway portion 530a, located at the apparatus 500' inlet side 540a, is connected to the apparatus 500' enclosure 560 and the other end of the first gas pathway portion 530a is connected with the microparticle counter 510. One end of the second gas pathway portion 530b is connected to the microparticle counter 510. The other end of the second gas pathway portion 530b is not connected to any component and is inside of the gas reservoir 550. One end of the third gas pathway portion 530c is not connected to any component and is inside of the gas reservoir 550. The other end of the third gas pathway portion 530c is connected to the vacuum pump 520. One end of the fourth gas pathway portion 530d is connected to the vacuum pump 520 and the other end of the fourth gas pathway portion 530d is connected to the apparatus 500' wall at the outlet side 540b.

As depicted in FIG. 5, the second gas pathway portion 530b and the third gas pathway portion 530c are not connected to each other. For example, each of the second and third gas pathway portion 530cs has a respective end inside of the gas reservoir 550 that is not connected to any component. According to one embodiment, the gas reservoir 550 depicted in FIG. 5, is air tight and can function even if the vacuum pump 520 is outside of the apparatus 500.

Figure 6:
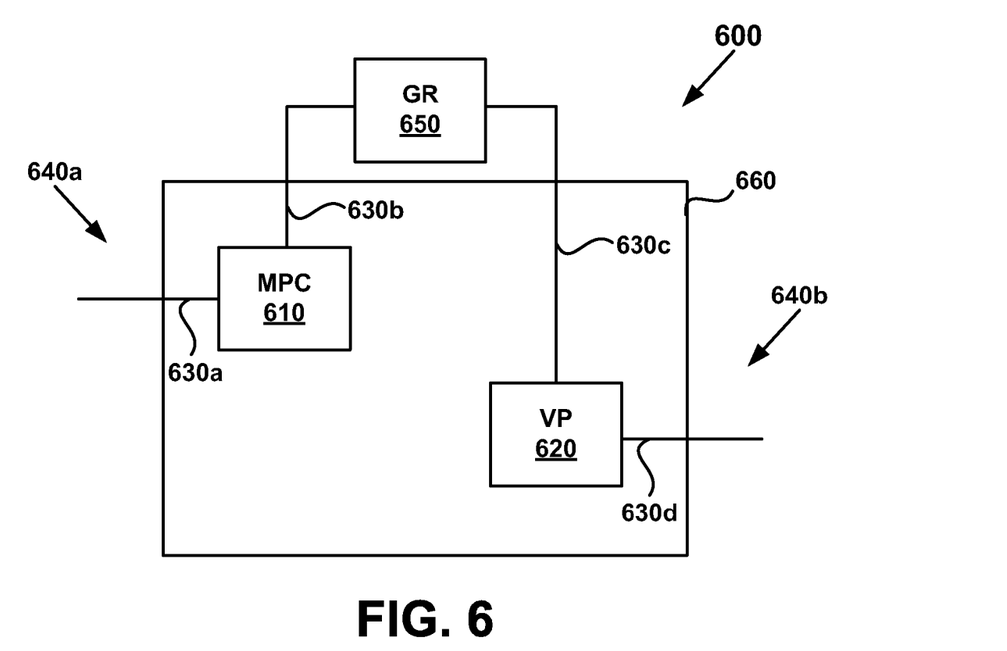
FIG. 6 depicts a block diagram of a microparticle measurement apparatus, according to one embodiment.

FIG. 6 depicts a block diagram of a microparticle measurement apparatus 600, according to one embodiment. As depicted in FIG. 6, the apparatus 600 includes a microparticle counter 610, a vacuum pump 620 and enclosure 660. The microparticle counter 610 and the vacuum pump 620 are inside of the enclosure 660. The apparatus 600 may include one or more external fittings, located at the apparatus 600's enclosure 660, for connecting a gas reservoir 650, which is outside of the enclosure 660.

One end of the first gas pathway portion 630a, located at the apparatus 600's inlet side 640a, is connected to the apparatus 600's enclosure 660 and the other end of the first gas pathway portion 630a is connected to the microparticle counter 610. One end of the second gas pathway portion 630b is connected to the microparticle counter 610 and the other end to the second gas pathway portion 630b is connected to a first external fitting of the apparatus 600. One end of a third gas pathway portion 630c is connected to a second external fitting of the apparatus 600. The other end of the third gas pathway portion 630c is connected to the vacuum pump 620. One end of a fourth gas pathway portion 630d is connected to the vacuum pump 620 and the other end of the fourth gas pathway portion 630d is connected with the apparatus 600's enclosure 660 at the outlet side 640b.

According to one embodiment, a gas reservoir 650, which is outside of the apparatus 600's enclosure 660, can be coupled with the apparatus 600 at the first and second external fittings. According to one embodiment, the external gas reservoir 650 may or may not be an integral part of the apparatus 600. As depicted in FIG. 6, the gas reservoir 650 is located at a portion of a gas pathway that is between the microparticle counter 610 and the vacuum pump 620.

The blocks that represent features in FIGS. 3-6 can be arranged differently than as illustrated, and can implement additional or fewer features than what are described herein. Further, the features represented by the blocks in FIGS. 3-6 can be combined in various ways. The apparatuses 300-600 can be implemented using hardware, hardware and software, hardware and firmware, or a combination thereof.

According to one embodiment, the gas reservoir serves to increase the capacity of the gas pathway. According to one embodiment, the shape of the gas reservoir is not important.

Figure 7:
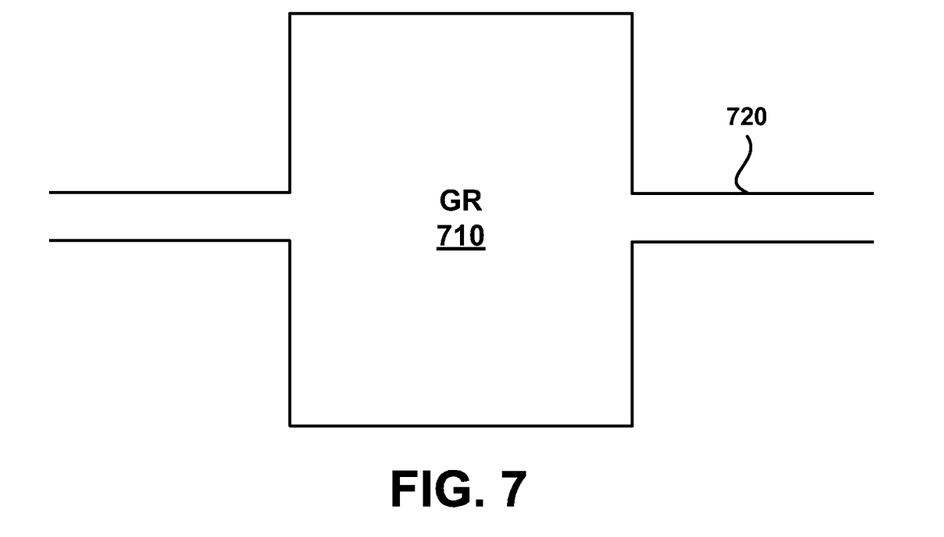
FIGS. 7-9 depict gas reservoirs, according to various embodiments.

FIG. 7 depicts a gas reservoir, according to one embodiment. According to one embodiment, the gas reservoir 710 is part of a gas pathway portion 720, associated with a microparticle measurement apparatus, and has a larger diameter than the rest of the gas pathway portion 720. As depicted in FIG. 7, the gas reservoir is located in line with the gas pathway.

Figure 8:
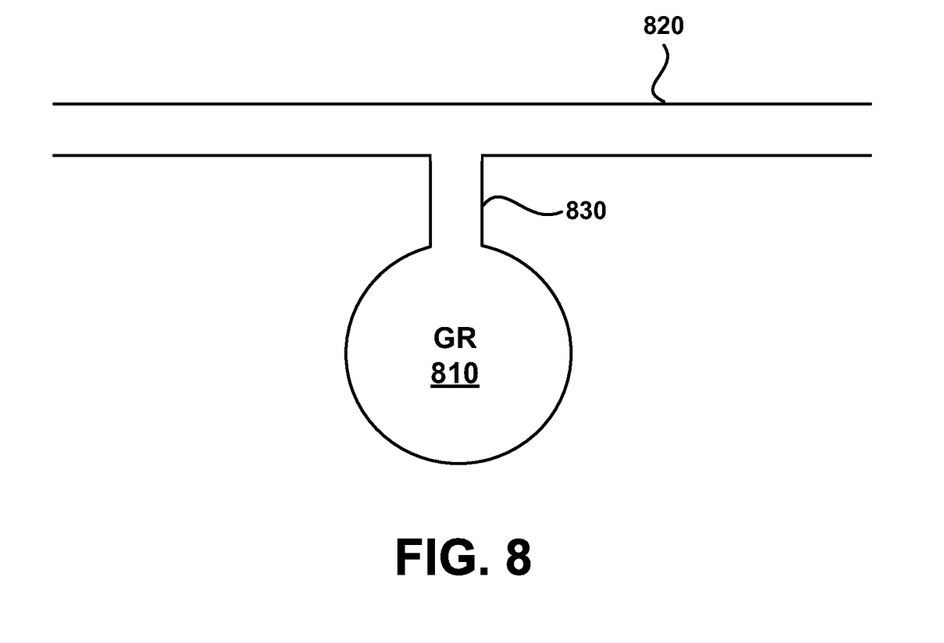

FIG. 8 depicts a gas reservoir, according to one embodiment. According to one embodiment, the gas reservoir 810 is a cylindrical shaped component. As depicted in FIG. 8, the gas reservoir 810 is not in line with gas pathway portion 820 associated with a microparticle measurement apparatus. For example, the gas reservoir 810 is located at a branch 830 of the gas pathway portion 820.

Figure 9:
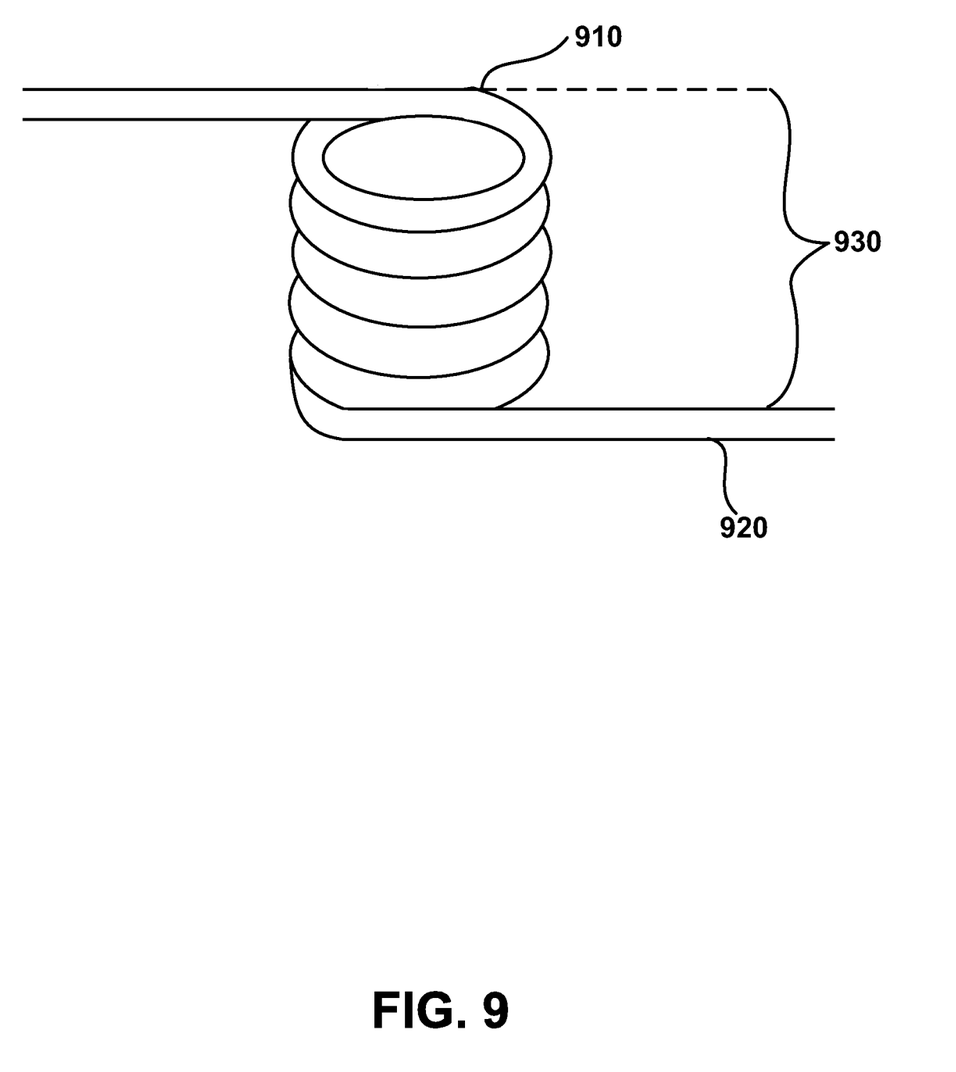

FIG. 9 depicts a gas reservoir, according to one embodiment. According to one embodiment, the gas reservoir 910 is a long coiled portion 930 of a gas pathway portion 920 associated with a microparticle measurement apparatus. According to one embodiment, the long coiled portion 930 is at least 10 meters (m) long.

According to one embodiment, a gas reservoir, according to one embodiment, is air tight or partially air tight. A component, such as a vacuum pump or a gas reservoir, that is located outside of the apparatus' enclosure may or may not be a part of the apparatus.

An apparatus can include one or more external fittings for connecting a vacuum pump or a gas reservoir, which is not inside of the apparatus' enclosure. According to one embodiment, an external gas reservoir or an external vacuum pump may or may not be an integral part of the apparatus. According to one embodiment, the gas reservoir is located at a portion of a gas pathway that is between the microparticle counter and the vacuum pump even when the gas reservoir or the vacuum pump is located outside of the apparatus' enclosure.

According to one embodiment, a gas pathway portion may go through the wall of a component or may appear to go through the wall of a component. Various embodiments are well suited to implementing a gas pathway portion, for example, using two tubes that are coupled on each side of that component's wall. According to one embodiment, there may be external fittings located at the inlet side or the outlet side of the apparatus at the location of corresponding gas pathway portions.

According to one embodiment, portions of the gas pathway may be located outside of the apparatus' enclosure. For example, various embodiments are well suited for locating a gas reservoir as depicted in any of FIG. 7, 8, or 9 or a vacuum pump outside of the apparatus' enclosure.

Various embodiments provide for increasing the stability of air pressure using a gas reservoir where the air pressure instability is introduced, for example, at the inlet side. This can level the amount of inflow to an apparatus, according to various embodiments, providing a more accurate dust particle count compared to conventional apparatuses. Various embodiments provide the most accurate measurements when the nozzle's tip is in close proximity with an electronic item's surface that is being measured, for example, with little or no gap between the nozzle's tip and the electronic item's surface. Various embodiments provide for increasing the lifespan of the apparatus due, for example, to reduced fluctuations in the air flow rate to the vacuum pump, reduced load on the vacuum pump, and reduced obstructions of the gas pathway. Various embodiments provide for increased control of the air flow rate and increased control in the production process. For example, the technicians can focus more on other tasks in progress and at the same time, the apparatus does not use or does not require a pressure compensation mechanism, according to one embodiment. For at least this reason, according to various embodiments, the apparatus can be simplified in comparison to conventional apparatus, thus, providing a cost savings.

The following illustrates a theoretical simulation of a microparticle measurement apparatus, according to various embodiments. Gas, such as air, generally conforms to what is considered to be the gas law as follows:

$$PV = nRT \quad \text{(eq 1)}$$

where P is pressure of a gas, V is the volume of the gas, R is the gas constant, n is the amount of substance of gas, and T is the temperature of the gas.

When the temperature is deemed to be fixed, the right-hand side of equation 1 is a constant.

$$PV = C \quad \text{(eq 2)}$$

When both sides are differentiated, $$dP/dt \cdot V + P \cdot dV/dt \quad \text{(eq 3)}$$

$$dP/dt = -P/V \cdot dV/dt \quad \text{(eq 4)}$$

The pressure fluctuation is proportional to PN, according to one embodiment.

In this illustration of the theoretical simulation of a microparticle measurement apparatus, the microparticle measurement apparatus is assumed to have an air flow rate of 1 cubic feet per minute (cfm). The following shall discuss two postulated cases. The first case involves a conventional microparticle apparatus without a gas reservoir that includes a microparticle counter and a vacuum pump connected by a gas pathway that has a diameter of 1 centimeter (cm) and a length of 5 cm. When separate components are simply connected, this value can be reduced; however, a fairly large value is assumed within the range that can be hypothesized.

The second case involves a microparticle apparatus that includes a gas reservoir, a microparticle counter and a vacuum pump connected by a gas pathway that has a diameter of 1 cm and a length of 5 cm. When separate components are simply connected, this value can be reduced; however, a fairly large value is assumed within the range that can be hypothesized. In this second case, the gas reservoir is assumed to have a 500 cc capacity.

The volume of the gas pathway, in the conventional microparticle apparatus without the gas reservoir, is 3.9 cc. In contrast, the volume of the gas pathway, when the apparatus includes a 500 cc gas reservoir, is 503.9 cc.

Regardless of the value of pressure P, the value of PV is proportional to the reciprocal of the value already obtained. For example, the magnitude of the value for a conventional apparatus without a gas reservoir is approximately 100. In contrast, the magnitude of the value for an apparatus with a gas reservoir, according to various embodiments, has a relationship of approximately 0.8. According to one embodiment, it is possible to restrict momentary fluctuations in air pressure to less than 1 percent. For example, according to one embodiment, it is possible to restrict momentary fluctuations in air pressure to 0.8 percent. When the capacity of the gas reservoir is assumed to be 300 cc, it is possible to restrict momentary fluctuations in air pressure to approximately 1.3 percent.

The vacuum pump may have to suction surplus gas in proportion to the capacity of the gas reservoir. However, calculations based on the assumption that the capacity of the gas reservoir is 500 cc indicate that it takes approximately 1 second to suction the 500 cc of gas with an air flow rate of 1 cfm. Consequently, the simulation indicates that the impact of possible surplus gas due to a gas reservoir is negligible.

Although the simulation of an apparatus, according to various embodiments, assumed certain measurements of components, such as certain diameters, lengths, capacities, among other things, various embodiments are well suited for other measurements. Although a simulation of an apparatus, according to various embodiments, assumed a gas reservoir with a capacity of 500 cc, various embodiments are well suited to gas reservoirs with other capacities.

Although various embodiments have been described in the context of using an apparatus in quality control, an apparatus, according to various embodiments, can be used for other purposes, such as environmental purposes. For example, an apparatus can be used for measuring fibers, such as asbestos. In another example, an apparatus can be used for measuring a level of cleanliness.

Example embodiments of the subject matter are thus described. Although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

Various embodiments have been described in various combinations and illustrations. However, any two or more embodiments or features may be combined. Further, any embodiment or feature may be used separately from any other embodiment or feature. Phrases, such as "an embodiment," "one embodiment," among others, used herein, are not necessarily referring to the same embodiment. Features, structures, or characteristics of any embodiment may be combined in any suitable manner with one or more other features, structures, or characteristics.

What is claimed is:

1. A microparticle measurement apparatus, wherein the apparatus comprises:
    a microparticle counter for counting a number of microparticles in a volume of gas received by the microparticle counter;
    a vacuum pump for causing the volume of gas to flow through the microparticle counter using negative pressure; and
    a gas reservoir for increasing stability of air pressure at the microparticle counter even when air pressure or air flow rate provided by a nozzle coupled to the microparticle measurement apparatus is unstable.

2. The microparticle measurement apparatus of claim 1, wherein the microparticle measurement apparatus includes an enclosure and wherein the gas reservoir is inside of the enclosure.

3. The microparticle measurement apparatus of claim 1, wherein the microparticle measurement apparatus includes an enclosure and wherein the gas reservoir is outside of the enclosure.

4. The microparticle measurement apparatus of claim 1, wherein the gas reservoir is inside of the microparticle counter.

5. The microparticle measurement apparatus of claim 1, wherein the microparticle measurement apparatus includes an enclosure that is used as the gas reservoir.

6. The microparticle measurement apparatus of claim 1, wherein the gas reservoir is part of a gas pathway portion, associated with the microparticle measurement apparatus, and has a larger diameter than the rest of the gas pathway portion.

7. The microparticle measurement apparatus of claim 1, wherein the gas reservoir is a cylindrical shaped component located at a branch of a gas pathway portion associated with the microparticle measurement apparatus.

8. The microparticle measurement apparatus of claim 1, wherein the gas reservoir is a long coiled portion of a gas pathway portion associated with the microparticle measurement apparatus.

9. The microparticle measurement apparatus of claim 1, wherein the gas reservoir is located between the microparticle counter and the vacuum pump.

10. A microparticle measurement apparatus, wherein the apparatus comprises:
    a microparticle counter for counting a number of microparticles in a volume of gas received by the microparticle counter;
    an external fitting for coupling with a vacuum pump, which is external to the microparticle measurement apparatus, for causing the volume of gas to flow through the microparticle counter using negative pressure; and
    a gas reservoir for increasing stability of air pressure at the microparticle counter even when air pressure or air flow rate provided by a nozzle coupled to the microparticle measurement apparatus is unstable.

11. The microparticle measurement apparatus of claim 10, wherein the microparticle measurement apparatus includes an enclosure and wherein the gas reservoir is inside of the enclosure.

12. The microparticle measurement apparatus of claim 10, wherein the microparticle measurement apparatus includes an enclosure and wherein the gas reservoir is outside of the enclosure.

13. The microparticle measurement apparatus of claim 10, wherein the gas reservoir is inside of the microparticle counter.

14. The microparticle measurement apparatus of claim 10, wherein the microparticle measurement apparatus includes an enclosure that is used as the gas reservoir.

15. The microparticle measurement apparatus of claim 10, wherein the gas reservoir is part of a gas pathway portion, associated with the microparticle measurement apparatus, and has a larger diameter than the rest of the gas pathway portion.

16. The microparticle measurement apparatus of claim 10, wherein the gas reservoir is a cylindrical shaped component located at a branch of a gas pathway portion associated with the microparticle measurement apparatus.

17. The microparticle measurement apparatus of claim 10, wherein the gas reservoir is a long coiled portion of a gas pathway portion associated with the microparticle measurement apparatus.

18. The microparticle measurement apparatus of claim 10, wherein the gas reservoir is located at a portion of a gas pathway that is between the microparticle counter and the vacuum pump.

19. A microparticle measurement apparatus, wherein the apparatus comprises:
    a microparticle counter for counting a number of microparticles in a volume of gas received by the microparticle counter;
    a vacuum pump for causing the volume of gas to flow through the microparticle counter using negative pressure; and an external fitting for coupling with a gas reservoir for increasing stability of air pressure at the microparticle counter even when air pressure or air flow rate provided by a nozzle coupled to the microparticle measurement apparatus is unstable.

20. The microparticle measurement apparatus of claim 19, wherein the gas reservoir is part of a gas pathway portion, associated with the microparticle measurement apparatus, and has a larger diameter than the rest of the gas pathway portion.

21. The microparticle measurement apparatus of claim 19, wherein the gas reservoir is a cylindrical shaped component located at a branch of a gas pathway portion associated with the microparticle measurement apparatus.

22. The microparticle measurement apparatus of claim 19, wherein the gas reservoir is a long coiled portion of a gas pathway portion associated with the microparticle measurement apparatus.

23. The microparticle measurement apparatus of claim 19, wherein the gas reservoir is located at a portion of a gas pathway that is between the microparticle counter and the vacuum pump.

* * * * *